United States Patent [19]

Buechele et al.

[11] Patent Number: 4,927,978
[45] Date of Patent: May 22, 1990

[54] METHOD OF PURIFYING BISPHENOLS

[75] Inventors: James L. Buechele; Edward L. Nielsen, both of Houston, Tex.; Walter Dong, Gold River, Calif.; Paul V. Shaw, Houston, Tex.

[73] Assignee: Shell Oil Company, Houston, Tex.

[21] Appl. No.: 285,253

[22] Filed: Dec. 16, 1988

[51] Int. Cl.$^5$ .................. C07C 37/84; C07C 37/68
[52] U.S. Cl. .................... 568/724; 568/749
[58] Field of Search ............ 568/724, 727, 749, 729

[56] References Cited

U.S. PATENT DOCUMENTS

| | | | |
|---|---|---|---|
| 2,791,616 | 5/1957 | Luten, Jr. | 260/619 |
| 3,535,389 | 10/1970 | DeJong | 260/619 |
| 3,936,507 | 2/1976 | Ligorati et al. | 260/619 |
| 3,972,950 | 8/1976 | Kwantes | 260/619 |
| 4,192,955 | 3/1980 | Reinitz | 568/724 |
| 4,209,646 | 6/1980 | Gae | 568/724 |
| 4,294,993 | 10/1981 | Li | 568/724 |
| 4,492,807 | 1/1985 | Aneja | 568/724 |
| 4,638,102 | 1/1987 | Little | 568/724 |

FOREIGN PATENT DOCUMENTS

| | | | |
|---|---|---|---|
| 0123210 | 10/1984 | European Pat. Off. | 568/724 |
| 2548470 | 5/1976 | Fed. Rep. of Germany | 568/724 |
| 798085 | 1/1981 | U.S.S.R. | |
| 924232 | 4/1963 | United Kingdom | 568/724 |
| 1536767 | 12/1978 | United Kingdom | 568/727 |

Primary Examiner—Werren B. Lone

[57] ABSTRACT

A process for the preparation of crystals of an adduct of a bisphenol with a phenol which comprises:

(a) adding an inert volatile liquid hydrocarbon diluent and 0–1.5% weight water to a crude mixture of the bisphenol and the phenol at a temperature above the boiling temperature of the added volatile liquid diluent; and (b) allowing the volatile liquid diluent to boil in the process, thereby cooling the resulting mixture of bisphenol and phenol to a temperature at which adduct crystals form.

29 Claims, No Drawings

METHOD OF PURIFYING BISPHENOLS

BACKGROUND OF THE INVENTION

1. Field of the Invention

The present invention relates to a process for the purification of bisphenols.

2. State of the Art

The purification of bisphenols by adduct crystallization has been practiced for some time with considerable variation. U.S. Pat. No. 2,791,616 discloses a process for crystallizing a bisphenol adduct and extracting the bisphenol with added water but this requires excessive amounts of water to produce increased yield. U. S. Pat. No. 3,936,507 discloses the crystallization of dried crude bisphenol with certain solvents in certain ratios. U.S. Pat. No. 4,192,955 discloses a process for crystallizing a bisphenol from a solution in a solvent in which the bisphenol is soluble and which is miscible with water. U.S. Pat. No. 3,535,389 discloses crystallization from a two-phase mixture containing water and an organic solvent. U.S. Pat. No. 4,294,993 discloses treating bisphenol adduct with toluene or toluene and water, heating and cooling but toluene is too miscible with phenol to serve as an inert diluent coolant. Russian patent No. 798,085 discloses the use of an organic solvent added prior to condensation, such as 50% toluene or benzene and optionally residual water. U.S. Pat. No. 4,209,646 describes a process for crystallizing a hot bisphenol adduct from a solution thereof in aqueous phenol by evaporating water to cool the liquid mixture at very reduced pressure to a point corresponding to the vapor pressure of the reaction mixture but this requires impractical amounts of energy to lower the pressure to the necessary very low level. Also, the patent states that the water content is critical and should be between 2–12% weight and, preferably, 4–8% weight. U.S. Pat. No. 4,492,807 discloses a process for crystallizing a bisphenol adduct from a liquid mixture which includes water and an organic liquid which will not react with the bisphenol or phenol and is a solvent for dissolving a substantial portion of the impurities or by-products resulting from the formation of the bisphenol. The process allows crystallization at lower temperature. However, some of the solvents would likely introduce impurities and Applicants have found that the use of solvents of the patent to remove impurities did not lead to an increase in purity, size or processability of the adduct crystals.

Despite the many varied processes, including those described above, there is still a need to develop a process for the recovery of a bisphenol which provides high purity crystals of bisphenol adduct which are large and firm so that they are easier to wash and otherwise work up because they do not break in handling. It is also desirable to reduce the use of pump-circulated surface heat exchange systems and the problems associated with such surface heat exchange systems, including fouling, breaking of crystals, and induced nucleation of the crystals making them difficult to filter.

SUMMARY OF THE INVENTION

The present invention is directed to a process for the preparation of crystals of an adduct of a bisphenol with a phenol which comprises:

(a) adding 8–25% weight of an inert volatile liquid aliphatic hydrocarbon diluent and 0–1.5% weight water to a crude mixture of the bisphenol and the phenol at a temperature above the boiling temperature of the added volatile liquid diluent; and (b) allowing the added volatile liquid diluent to boil in the process thereby cooling the resulting mixture from (a) to a temperature at which crystals of the adduct form.

The process of the invention provides a useful and efficient means of obtaining an adduct of a bisphenol by a crystallization process in which the heat of crystallization of the adduct is removed, preferably without the direct contact with an external cooling means, such as direct surface heat exchange devices, and their associated problems while providing crystals of the desired adduct, which are increased in desirable size, purity and processability.

DETAILED DESCRIPTION OF THE INVENTION

Any liquid can be used as the inert volatile liquid aliphatic hydrocarbon diluent which is inert to the other ingredients, has a boiling point below the boiling point of the phenol, is stable and which does not substantially dissolve or would not be dissolved in the bisphenol (i.e., a solubility for bisphenol at 25° C. of about 500 ppm or less, preferably 300 ppm or less) or the bisphenol by-product impurities (i.e., a solubility at 25° C. of less than about 0.1% weight of the impurities, or even less than 0.03% weight. Examples of suitable liquid diluents include aliphatic hydrocarbons such as butanes, pentanes, hexanes, heptanes, and the like. Such materials usually have a solubility in the mother liquor of about 8–20% weight, preferably about 10–15% weight at about 45° C. Operating at about the saturation point of the solvent in the mother liquor is useful. Preferably, the inert volatile liquid hydrocarbon diluent is an aliphatic hydrocarbon containing from 4 to 6 carbon atoms, especially pentane.

The amount of inert volatile liquid hydrocarbon diluent used can readily be determined by those skilled in the art for the particular size and kind of process used. By way of illustration, the amount of the inert volatile liquid hydrocarbon diluent can be from about 8 to about 25% weight based on the total mixture of ingredients present in the crystallizer and, preferably, from about 10 to about 20% weight and, especially, from about 10 to about 15% weight based on the total mixture.

The present invention is useful for the purification of bisphenols from the conventional preparation of bisphenols from a ketone and a phenol in the presence of an acid or an acidic acting material, including inorganic or organic materials in liquid or solid form. The bisphenols include those prepared by the reaction of a ketone, such as acetone, ethyl methyl ketone, isobutyl methyl ketone, acetophenone, cyclohexanone, 1,3-dichloroacetone and the like, with a phenol, such as phenol, o-cresol, m-cresol, o-chlorophenol, m-chlorophenol, o-t-butylphenol, 2,5-xylenol, 2,,5-di-t-butylphenol, o-phenylphenol and the like. The above is not meant to limit the invention but to illustrate representative examples of ketones and phenols which are known in the art to make desirable bisphenols and for which those of skill in the art can substitute other conventional bisphenol reactants.

A typical feed stream to the crystallizer is a product from the conventional condensation of a carbonyl compound, such as acetone with phenol to form bisphenol A (BPA) and usually contains from about 15 to about 60% weight of the bisphenol A, preferably 15-25% weight, and the remainder unreacted acetone or phenol and by-products of the reaction, including undesired isomers of the desired bisphenol A, higher condensation products, water and the like. Usually, the bisphenol A product is distilled to remove acetone, water and excess phenol so that the feed stream contains about 35% bisphenol A and about 65% phenol and impurities.

While the process can be conducted in the presence of less than about 1.5% by weight of water, preferably, less than about 1% weight, or in the absence of water, the use of a small amount of water in the range of from about 0.25 to about 1.5% weight based on the mother liquor to the crystallizer, preferably from about 0.3 to about 1.0% weight, will usually result in larger crystals. Use of the lower amounts of water could result in a somewhat smaller crystal size than if the higher amounts of water are used. Higher amounts of water result in a lower freezing point of the bisphenol and therefore lower operating temperatures.

The temperature of the process is sufficiently high to provide for the boiling of the volatile liquid and yet cool enough by boiling of the volatile liquid, preferably in the absence of external cooling means, for the crystallization of the desired adduct. By way of illustration, when using hexane, the temperature is conveniently between about 40° C. and 70° C. and, preferably between about 45° C. and 65° C. Operating at the lower range of temperatures could result in less impurities.

The pressure of the process is determined by the standard vapor pressure curve for the composition of the crystallizer admixture containing the volatile liquid diluent (and any water,) and the temperature of the crystallizer and generally does not require that the pressure of the process be extremely high. By choice of conditions, the process can be operated without substantially reducing the pressure below atmospheric pressure. The pressure can usually be about atmospheric pressure but can be any pressure at which the volatile liquid diluent (and any water) can function in the manner previously described to produce the desired cooling. By way of illustration, when using hexane as the volatile liquid and water in the amounts described above, the pressure can be from slightly less than about atmospheric, e.g., about 5 to about 50 psia, preferably about 5 to 20 psia; butanes would require from about 40 to about 170 psia. At the same diluent and water concentrations, pentanes would require higher pressures than hexane of from about atmospheric to about 90 psia, preferably to about 40 psia, while heptanes and the like would require lower pressures than hexane of from about 2 to 20 psia, preferably to about 6 psia. The use of atmospheric pressure ±10 psi is preferred.

The inert volatile liquid aliphatic hydrocarbon diluent can also serve a side benefit of reducing the density of the mother liquor and therefore improving the ability to separate the adduct crystals by centrifugation. It also lowers mother liquor viscosity.

The process can be conducted as a batch process or, preferably as a continuous process. One of skill in the art can readily adjust the rate of mixing and residence time to achieve the desired adduct crystals. Larger crystals are usually favored by longer residence times.

The adduct is recovered by conventional techniques known in the art as by filtration or, preferably by centrifugation or the like. Adduct crystallization can be conducted in one or more stages, with washing and redissolving in hot phenol between stages. The bisphenol is recovered from the adduct crystals by distillation of the phenol and cooling of the resulting molten bisphenol to a solid. Further purification can be accomplished by the same or another conventional crystallization method.

The mother liquor obtained after recovery of the adduct can be further crystallized to obtain residual bisphenol. Usually it is desirable to treat this mother liquor to remove excess aqueous phenol prior to the further crystallization. The mother liquor is then recycled with diluent (pentane) removal to the condensation reactor or used as a wash for earlier stage adduct crystals.

The inert volatile liquid is recovered by conventional procedures of condensation and the condensed volatile liquid is preferably recycled to the crystallization zone.

ILLUSTRATIVE EMBODIMENTS

The invention is illustrated by the following embodiments which should not be regarded as limiting it in any way.

EMBODIMENT 1

A 17-gallon, continous stirred tank crystallizer (CSTC) operated with the stirrer at 120-700 rpms was continuously injected with a crude mixture of phenol or bisphenol A mother liquor containing from 19-23% weight of bisphenol acetone, also known as bisphenol A (BPA). A second continuous feed of inert volatile liquid diluent, hexane, equal to from 9-13% weight based on the total ingredients of the crystallizer admixture was added and the water content was varied based on the total feed to the crystallizer. The temperature was maintained at 48°-60° C. and the residence time was 1-8 hours. The pressure was 10 psia. The hexane vapor from the reflux cooling was condensed and recycled. The adduct crystals were recovered by filtering slurry samples under isothermal conditions and quickly washing them with toluene to displace the mother liquor holdup. Air was drawn through the cake to vaporize the toluene and the dried cake was weighed to give a conservative measure of the slurry concentration. Some of these cakes were analyzed for purity and size distribution. Results of experiments conducted under these conditions are set forth in Table 1 below.

TABLE 1

Results Using Hexane

| | | | | |
|---|---|---|---|---|
| Run No. | 20 | 21 | 22 | 24 |
| Feed No. | 3 | 3 | 3 | 3 |
| Combined Feed Composition, % W | | | | |
| Phenol | 66.1 | 66.9 | 68.7[3] | 66.7 |
| BPA | 20.7 | 20.9 | 20.6 | 20.9 |
| OP-BPA[2] | 2.0 | 2.0 | 2.0 | 2.0 |
| Total Impurities[4] | 3.0 | 3.0 | 3.0 | 3.0 |
| H$_2$O | 0.58 | 0.55 | 1.0 | 0.58 |
| Hexane | 9.6 | 8.7 | 9.6 | 8.8 |
| Stage 1 Results | | | | |
| Conditions | | | | |
| Temp., °C. | 60 | 60 | 60 | 60 |
| Residence Time, Hr | 2.1 | 1.5 | 2.1 | 1 |
| Mixer RPM | 700 | 700 | 700 | 700 |
| Adduct Analysis, PPM, Phenol-Free Basis | | | | |
| OP-BPA | 267 | 301 | — | 334, 420 |
| Total Impurities[4] | 544 | 593 | — | 609, 734 |
| Slurry Conc., 1st stage | | | | |

TABLE 1-continued

| Results Using Hexane | | | | |
|---|---|---|---|---|
| % W | 11.2 | 11 | 9.8 | 11.4 |
| Estimated Average Crystal Size | | | | |
| Width (Visual) | 150 | 150 | 150 | 100 |
| Stage 2 Results | | | | |
| Temp., °C. | 48 | 48 | 48 | 48 |
| Adduct Analysis, PPM, Phenol-Free Basis | | | | |
| OP-BPA | 332 | 355 | —(1) | — |
| Total Impurities(4) | 624 | 655 | — | — |
| Slurry Conc., 2nd stage | | | | |
| % W | 20.8 | 17.6 | — | — |

(1)No test.
(2)o,p'-isomer of BPA.
(3)Includes impurities.
(4)Includes OP-BPA.

Results of the above experiments demonstrate that crystals of bisphenol A adduct were very pure and of increased size (width 75–150 microns vs 50 microns by conventional surface cooling processes) while the heat of crystallization due to adduct formation was removed without the use of direct contact with an external heat exchanger system.

EMBODIMENT 2

Experiments similar to those described in Embodiment 1 were conducted utilizing water and pentane.

The function of pentane in the above experiments was primarily to remove heat of adduct crystallization by vaporization instead of by use of direct contact with an external surface cooling means. Pentane also acts as an inert diluent (due to limited solubility in phenol) and lowers the cloud point of the crystallizing mixture by approximately 8° C. in the relative absence of water. The end crystallization temperatures are lowered proportionately and adduct recovery remains about the same.

What is claimed is:

1. A process for the preparation of crystals of an adduct of a bisphenol with a phenol which comprises:
   (a) adding 8–25% weight of an inert volatile liquid aliphatic hydrocarbon diluent and 0 to about 1.5% w water to a crude mixture of the bisphenol and the phenol at a temperature above the boiling temperature of the added volatile liquid diluent; and
   (b) allowing the volatile liquid diluent to boil in the process thereby cooling the resulting mixture to a temperature at which crystals of the adduct form.

2. A process according to claim 1 wherein the inert volatile liquid hydrocarbon diluent is an aliphatic hydrocarbon containing 4 to 6 carbon atoms.

3. A process according to claim 2 wherein less than about weight water is present in the resulting mixture.

4. A process according to claim 3 wherein the inert volatile liquid hydrocarbon diluent is butane or hexane.

5. A process according to claim 3 wherein the inert volatile liquid hydrocarbon diluent is pentane.

6. A process according to claim 1 wherein about 0.25 to about 1.5% weight water is present based on the mother liquor.

7. A process according to claim 6 wherein about 0.3 to about 1.0% weight water is present.

8. A process according to claim 1 wherein the bisphenol is bisphenol A.

9. A process according to claim 8 wherein the inert volatile liquid hydrocarbon diluent is an aliphatic hydrocarbon containing 4 to 6 carbon atoms.

10. A process according to claim 9 wherein less than about 1% weight water is present based on the mother liquor.

11. A process according to claim 10 wherein the inert volatile liquid hydrocarbon diluent is butane or hexane.

12. A process according to claim 10 wherein the inert volatile liquid hydrocarbon diluent is pentane.

13. A process according to claim 12 wherein about 0.25 to about 1.5% weight water is present in the mother liquor.

14. A process according to claim 13 wherein about 0.3 to 1.0% about weight water is present.

15. A process according to claim 11 wherein about 0.25 to about 1.5% weight water is present in the mother liquor.

16. In a process for the purification of a crude bisphenol by adduct crystallization with a phenol, the improvement which comprises conducting the adduct crystallization by (a) adding to a mixture of crude bisphenol and a phenol an inert volatile organic diluent and 0 to about 1.5% weight water at a temperature above the boiling temperature of the diluent and (b) allowing the diluent to boil in the process thereby cooling the resulting mixture to a temperature at which crystals of the adduct form.

17. A process according to claim 16 wherein the inert volatile liquid hydrocarbon diluent is an aliphatic hydrocarbon containing 4 to 6 carbon atoms.

18. A process according to claim 17 wherein less than about 1% weight water is present in the mother liquor.

19. A process according to claim 18 wherein the inert volatile liquid hydrocarbon diluent is pentane.

20. A process according to claim 16 wherein about 0.25 to about 1.5% weight water is present based on the mother liquor.

21. A process according to claim 20 wherein about 0.3 to about 1.0% weight water is present.

22. A process according to claim 16 wherein the bisphenol is bisphenol A.

23. A process according to claim 22 wherein the inert volatile liquid hydrocarbon diluent is an aliphatic hydrocarbon containing 4 to 6 carbon atoms.

24. A process according to claim 23 wherein less than about 1% weight water is present based on the mother liquor.

25. A process according to claim 24 wherein the inert volatile liquid hydrocarbon diluent is butane or hexane.

26. A process according to claim 24 wherein the inert volatile liquid hydrocarbon diluent is pentane.

27. A process according to claim 26 wherein about 0.25 to about 1.5% weight water is present in the mother liquor.

28. A process according to claim 27 wherein about 0.3 to 1.0% about weight water is present.

29. A process according to claim 25 wherein about 0.25 to about 1.5% weight water is present in the mother liquor.

* * * * *